United States Patent [19]
Asselin et al.

[11] 4,057,559
[45] Nov. 8, 1977

[54] CARBAZOLE ACETIC ACID DERIVATIVES

[75] Inventors: Andre A. Asselin, Lemoyne; Leslie G. Humber; Thomas A. Dobson, both of Dollard des Ormeaux, all of Canada

[73] Assignee: American Home Products Corporation, New York, N.Y.

[21] Appl. No.: 575,552

[22] Filed: May 7, 1975

Related U.S. Application Data

[63] Continuation-in-part of Ser. No. 402,240, Oct. 1, 1973, abandoned.

[51] Int. Cl.² .................................... C07D 209/86
[52] U.S. Cl. .............................. 260/315; 260/250 C; 260/326.27; 260/340.9 R; 260/514 K; 560/34; 560/122; 560/126; 424/274
[58] Field of Search ........................... 260/315, 326.27; 424/274

[56] References Cited

U.S. PATENT DOCUMENTS

| 3,868,387 | 2/1975 | Berger et al. | 260/315 |
| 3,896,145 | 7/1975 | Berger et al. | 260/315 |

OTHER PUBLICATIONS

Elderfield, Heterocyclic Compounds, 3:298-301, (1952).

Primary Examiner—Henry R. Jiles
Assistant Examiner—R. W. Ramsuer
Attorney, Agent, or Firm—Stephen Venetianer

[57] ABSTRACT

Tetrahydrocyclopent[b]indole-3-acetic acid, tetrahydrocarbazole-1-acetic acid and hexahydrocyclohept[b]indole-6-acetic acid derivatives in which the carbon bearing alkyl, lower alkenyl or lower cycloalkyl are disclosed. The compounds are useful antiinflammatory agents and methods for their preparation and use are described.

8 Claims, No Drawings

CARBAZOLE ACETIC ACID DERIVATIVES

This Application is a Continuation-in-Part of our earlier Application Ser. No. 402,240, filed October 1, 1973 and now abandoned.

BACKGROUND OF THE INVENTION a. Field of Invention

This invention relates to tricyclic acetic acid derivatives, to their preparation and use, and to intermediates used for their preparation.

More specifically, this invention relates to tricyclic acid derivatives in which the tricyclic portion therof is characterized by having an indole portion fused to a cyclopentane, cyclohexane or cycloheptane ring. Still more specifically, the compounds of this invention are characterized as derivatives of one of the following tricyclic acetic acid systems:

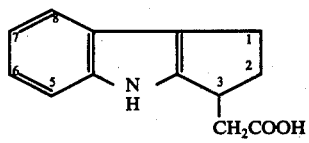

a. 1,2,3,4-tetrahydrocyclopent[b]indole-3-acetic acid,

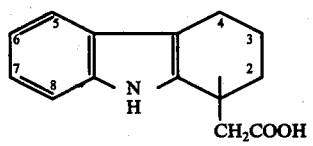

b. 1,2,3,4-tetrahydrocarbazole-1-acetic acid, or

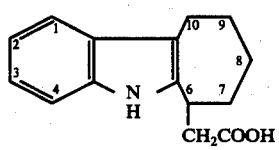

c. 5,6,7,8,9,10-hexahydrocyclohept[b]indole-6-acetic acid, in which the carbon bearing the acetic acid residue is further substituted with a lower alkyl, lower alkenyl or lower cycloalkyl.

The tricyclic acetic acid compounds of this invention possess useful pharmacologic properties; for instance, they exhibit antiinflammatory activity at dose levels which do not elicit undesirable side effects. The foregoing combination of attributes renders the compounds of this invention useful for the treatment of inflammatory conditions.

b. Prior Art

Apparently the closest prior art to the present invention is a report by H. Sakakibara and T. Kobayashi, Tetrahedron, 22, 2475 (1966), describing the preparation of 1,2,3,4-tetrahydrocarbazole-1-acetic acid. Pharmacologic properties for the compound are not mentioned. The latter compound is distinguished from the compounds of the present invention by its structural arrangement and its pharmacologic properties. More particularly, it is distinguished readily by the fact that it lacks a fully substituted carbon atom at position 1 of the carbazole-1-acetic acid system and secondly the compound lacks antiinflammatory activity when tested in standard pharmacologic tests, see below, in which the compounds of this invention exhibit substantial antiinflammatory effects.

Other prior art, although structurally further removed, includes a report by G. R. Allen, Jr., J. Heterocycl. Chem., 7, 239 (1970), describing the preparation of 1,2,3,4-tetrahydrocarbazole-2-carboxylic acid and its corresponding 6-methoxy derivative (see also Belgian Pat. No. 771598, issued Feb. 21, 1972).

SUMMARY OF THE INVENTION

The compounds of this invention are represented by formula 1,

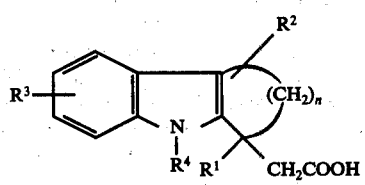

in which $R^1$ is lower alkyl, lower alkenyl or lower cycloalkyl, $R^2$ is hydrogen or lower alkyl, $R^3$ is hydrogen, lower alkyl, halo, hydroxy, lower alkoxy, lower alkanoyloxy or trihalomethyl, $R^4$ is hydrogen or lower alkyl and $n$ is an integer from two to four, with the proviso that $R^1$ is other than methyl when $R^2$ and $R^3$ are both hydrogen.

The compounds of this invention are prepared by a process in which the hydrazine of formula 2,

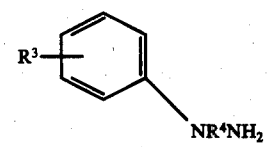

in which $R^3$ and $R^4$ are as defined herein is condensed with a compound of formula 3,

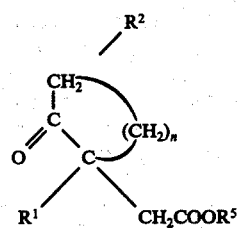

in which $R^1$, $R^2$ and $n$ are as defined herein and $R^5$ is hydrogen or lower alkyl to give the corresponding hydrazone of formula 4,

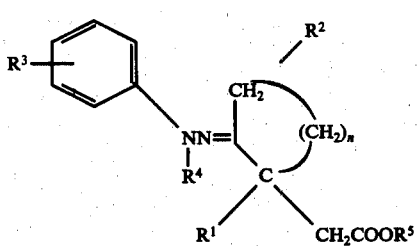

in which $R^1$, $R^2$, $R^3$, $R^4$, $R^5$ and $n$ are as defined herein. The hydrazone is then cyclized by treatment with a cyclizing agent to give the corresponding tricyclic compound of formula 5,

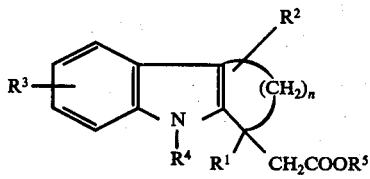

in which $R^1$, $R^2$, $R^3$, $R^4$, $R^5$ and $n$ are as defined herein; followed, when said compound of formula 5 is other than said compound of formula 1, by subjecting the compound of formula 5 to hydrolysis conditions to give the desired corresponding compound of formula 1.

In other words, whe $R^5$ of said compound of formula 5 is hydrogen, the compound is the desired compound of formula 1 and when $R^5$ of said compound of formula 5 is lower alkyl, the compounds of formula 5 is treated with a hydrolyzing agent to give the desired corresponding compound of formula 1.

DETAILED DESCRIPTION OF THE INVENTION

The term "lower alkyl" as used herein contemplates straight chain alkyl radicals containing from one to six carbon atoms and branched chain alkyl radical containing from three to four carbon atoms and includes methyl, ethyl, propyl, isopropyl, butyl, isobutyl, pentyl, hexyl and the like.

The term "lower alkenyl" as used herein contemplates straight chain alkenyl radicals containing from two to six carbon atoms and branched chain alkenyl radicals containing from three to four carbon atoms and includes vinyl, allyl, 1-propenyl, isopropenyl, 2-methylpropenyl and the like.

The term "lower cycloalkyl" as used herein contemplates saturated cyclic hydrocarbon radicals containing from three to six carbon atoms and includes cyclopropyl, cyclobutyl, cyclopentyl and cyclohexyl.

The term "lower alkoxy" as used herein contemplates both straight and branched chain alkoxy radicals containing from one to four carbon atoms and includes methoxy, ethoxy, isopropoxy, t-butoxy and the like.

The term "lower alkanoyloxy" as used herein contemplates both straight and branched chain alkanoyloxy radicals containing from two to six carbon atoms and includes acetoxy, propionyloxy, pivaloyloxy, hexnoyloxy and the like.

The term "halo" as used herein contemplates halogens and includes fluorine, chlorine, bromine and iodine.

The term "trihalomethyl" as used herein contemplates trifluoromethyl, trichloromethyl and tribromomethyl.

The compounds of formula 1 form salts with suitable pharmaceutically acceptable inorganic and organic bases. These derived salts possess the same activity as the parent acid and are included within the scope of this invention. The acid is transformed in excellent yield into the corresponding pharmaceutically acceptable salts by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di and trialkanolamines, the alkanol radicals of which contain up to three carbon atoms, such as mono-, di- and triethanolamine; alkylenediamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methylmorpholine and N-(2-hydroxyethyl)piperidine, as well as pyridine. Furthermoe, there may be mentioned the corresponding quaternary salts, such as the tetraalkyl (for example tetramethyl), alkyl-alkanol (for example methyltrimethanol andtrimethyl-monoethanol) and cyclic ammonium salts, for example the N-methyl-pyridinium, N-methyl-N-(2-hydroxyethyl)-morpholinium, N,N-dimethyl-morpholinium, N-methyl-N-(2-hydroxyethyl)-morpholinium, N,N-dimethylpiperidinium salts, which are characterized by a good water-solubility. In principle, however, there can be used all the ammonium salts which are physiologically compatible.

The transformations to the salts can be carried out by a variety of methods known in the art. For example, in the case of the inorganic salts, it is preferred to dissolve the selected acid in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the selected acid is dissolved in a suitable solvent of either moderate or low polarity, for example, ethanol, acetone, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the selected acid with an equivalent amount of the corresponding quaternary ammonium hydroxide in water solution, followed by evaporation of the water.

Also included within the scope of this invention are the isomers of the compounds of formula 1 resulting from the asymmetric centers contained therein.

Antiinflammatory Activity

The useful antiinflammatory activities of the tricyclic acetic acid derivatives are demonstrated in standard pharmacologic tests, for example, the tests described by R. A. Turner in "Screening Methods in Pharmacology," Academic Press, New York and London, 1965, pp. 152–163.

More particularly exemplified the antiinflammatory effect for the compounds of this invention is demonstrated readily in a modification of the established arthritis test in rats described by B. B. Newbould, Br. J. Parmac., 35, 487 (1969). In this test rats are made arthritic by treating them with an injection of Freund's adjuvant into the left hind paw. After 14 days (day 0 of test) a chronic arthritis is established. At this point the rats are treated with a uniform daily dose of the test compound from day 0 to day 8 of the test. Results are expressed as the change in volume of the injected paw from day 0. Untreated arthritic rats show an increased paw size whereas active compounds cause a reduction in the volume of the injected paw.

Typical results obtained for the compounds of the present invention in the aforementioned test are as follows:

| Compound | Daily Dose (mg/kg/p.o.) | Reduction of Paw Size (ml) |
|---|---|---|
| 1-ethyl-1,2,3,4-tetra-hydrocarbazole-1-acetic acid (Example 51) | 10 | 0.88 |
| 1-ethyl-8-isopropyl-1,2,3,4-tetrahydro-carbazole-1-acetic acid (Example 58) | 10 | 1.53 |
| 1,8-diethyl-1,2,3,4-tetra-hydrocarbazole-1-acetic acid (Example 56) | 10 | 1.19 |

In contrast the compound of the prior art, 1,2,3,4-tetrahydrocarbazole-1-acetic acid, showed no reduction of paw size at a daily dose of 10 or even 100 mg/kg/p.o. under the conditions of this test.

The lack of side effects for the compounds of this invention are demonstrated by standard acute toxicity tests (see Turner cited above) and by prolonged administration of the compound to warm-blooded animals.

When the compounds of this invention are employed as antiinflammatory agents in warm-blooded animals, e.g., rats, they are administered orally, alone or in dosage forms, i.e, capsules or tablets, combined with pharmacologically acceptable excipients, or they are administered orally in the form of solutions in suitable vehicles such as vegetable oils or water.

The doage of the indole derivatives of this invention will vary with the particular compound chosen and form of administration. Furthermore, it will vary with the particular host under treatment. Generally, the compounds of this invention are administered at a concentration level that affords protective effects without any deleterious side effects. These antiinflammatorily effective concentration levels are usually obtained within a therapeutic range of 1.0 mg to 500 mg/kg per day, with a preferred range of 10 to 100 mg/kg per day.

The compounds of this invention also possess analgesic and antipyretic activities.

The requisite starting materials of formula 2, phenylhydrazine or substituted phenylhydrazines are known or are prepared accoding to known methods. A convenient method for preparing the substituted phenylhydrazines involves the diazotization of the appropriately substituted aniline to give the corresponding diazo derivative. The latter compound is then reduced with stannous chloride or sodium sulfite to give the corresponding phenylhydrazine, see L. F. Fieser and M. Fieser, "Advanced Organic Chemistry", Reinhold Publishing Corporation, New York, 1961, p. 734.

the requisite starting materials of formula 3 are prepared by several methods. Three of these methods are illustrated in the following flow diagram in which $R^1$, $R^2$, and $R^5$ and n are as defined herein, $R^6$ is hydroxy or butylthio and $R^7$ is lower alkyl:

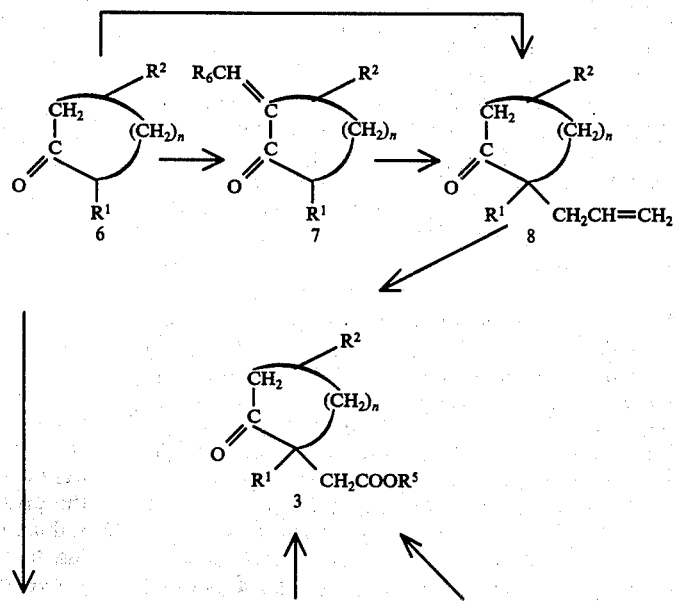

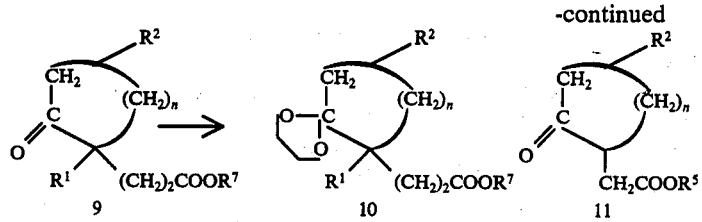

With reference to the first process for preparing the starting material, the substituted cycloalkanone of formula 6 is transformed into its corresponding hydroxymethylene derivative of formula 7 in which $R^1$, $R^2$ and n are as defined in the first instance and $R^6$ is hydroxy by treatment with ethyl formate in the presence of sodium hydride. In turn the hydroxymethylene derivative reacts readily with butanethiol to afford the corresponding butylthiomethylene derivative of formula 7 in which $R^1$, $R^2$ and n are as defined in the first instance and $R^6$ is butylthio. The latter compound is then subjected to alkylation with allyl bromide or allyl chloride in the presence of a proton acceptor, preferably sodium tertamylate or potassium tert-butoxide, to give the corresponding butylthiomethylene derivative of the ketone of formula 8. Subsequent removal of the butylthiomethylene blocking group by heating the latter derivative in aqueous diethyleneglycol with sodium or potassium hydroxide [see R. E. Ireland and J. A. Marshall, J. Amer. Chem. Soc., 81, 6336 [(1959)] yields the corresponding ketone of formula 8. The ketone of formula 8 is obtained alternatively by reacting the appropriate substituted cycloalkanone of formula 6 directly with allyl bromide or chloride in the presence of a strong proton acceptor, for example, sodium tert amylate, potassium tert-butoxide, sodamide, sodium hydride and the like, according to the method of J. M. Conia and F. Leyendecker, Bull. Soc. Chem. Fr., 830 (1967).

Oxidation of the ketone of formula 8 with ruthenium tetroxide-sodium metaperiodate according to the method of S. C. Welch and R. Y. Wong, Tetrahedron Letters, 1853 (1972) gives the desired starting material of formula 3 in which $R^5$ is hydrogen. Thereafter, if desired, the latter compound, a cycloalkanoneacetic acid derivative, is converted to its corresponding lower alkyl ester derivative of formula 3 by standard esterification methods; for example, by treatment with a lower alkanol in the presence of an acid, for instance, methanol and hydrogen chloride, or by treatment with an alkyl halide in the presence of a proton acceptor, for instance, methyl iodide and potassium carbonate.

Alternatively the desired starting material is obtained by condensing the aforementioned substituted cycloalkanone of formula 6 with methyl acrylate in the presence of potassium tert-butoxide according to the method of H. House and M. Schellenbaum, J. Org. Chem., 28, 34 (1963) to obtain the cycloalkanonepropionic acid lower alkyl ester of formula 9 in which $R^1$, $R^2$, and n are as defined hereinbefore and $R^7$ is lower alkyl. After conversion of the latter compound to its corresponding ethylene ketal derivative of formula IO with ethylene glycol and an acid catalyst, preferably p-toluenesulfonic acid, the ketal derivative is subjected to a Barbier-Wieland degradation according to the method of G. Stork, et al., J. Amer. Chem. Soc., 85, 3419 (1953). More specifically, the ketal 10 is first treated with an excess of phenyl magnesium bromide or chloride to give the corresponding diphenyl tertiary alcohol with on simultaneous deketalization and dehydration with aqueous acetic acid, and subsequent oxidation of the resulting keto olefin with ruthenium tetroxide-sodium metaperiodate in the same manner as described above gives the corresponding desired starting material of formula 3 in which $R^5$ is hydrogen. If desired the latter compound is converted to its corresponding lower alkyl ester by esterification in the manner described previously to give the desired starting material of formula 3 in which $R^5$ is lower alkyl.

Again alternatively a third method for preparing the starting material comprises the direct alkylation of the corresponding cycloalkanoneacetic acid lower alkyl ester of formula II in which $R^2$ and n are as defined above and $R^5$ is lower alkyl with the appropriate lower alkyl, lower alkenyl or lower cycloalkyl bromide, chloride or iodide in the presence of a suitable proton acceptor preferably sodium tert-amylate or potassium tert-butoxide, according to the method of Conia and Leyendecker, cited above, followed again by optional esterification as described above.

The substituted cycloalkanone utilized for the first two processes for preparing the starting material are either known, for example, 2-methylcyclohexanone and 2-ethylcyclohexanone or are prepared by known methods, for example, see "Rodd's Chemistry of Carbon Compounds," 2nd Ed., S. Coffey, Ed., Elsevier Publishing Company, Amsterdam, Vol. 2A, 1967, pp. 64 – 168 and Vol. 2B, 1968, pp. 92 – 113.

Likewise the cycloalkanoneacetic acid lower alkyl esters of formula II, required for the aforementioned methods are also known, for example, 1,4-dimethyl-2-cyclohexanone-1-acetic acid ethyl ester, see Welch and Wong, cited above, or they are prepared by known method, for example, see "Chemistry of Carbon Compunds," E. H. Rodd, Ed., Elsevier Publishing Co., Amsterdam, Vol. 2A, 1953, pp. 220 – 248.

Still another preparation of the compound of formula 3 is realized by subjecting an appropriately substituted 2-ketocycloalkaneacetonitrile of formula 12

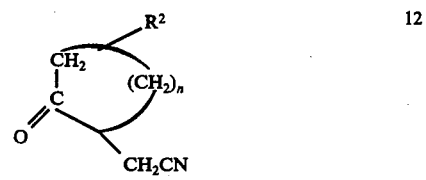

in which $R^2$ and n are as defined in the first instance to alkylation with the appropriate lower alkyl, lower alkenyl or lower cycloalkyl brmode, chloride or iodide in the presence of a suitable proton acceptor, preferably sodium tert-amylate or potassium tert-butoxide, according to the method of Conia and Leyendecker, cited above, to give the corresponding compound of formula 13

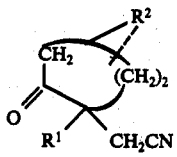

in which $R^1$, $R^2$ and n are as defined in the first instance. Thereafter the latter compound is subject to basic hydrolysis, preferably using sodium or potassium hydroxide as the base to give the corresponding starting material of formula 3.

The requisite 2-ketocycloalkaneacetonitriles are either known or are prepared by the method of G. Stork, et al., J. Amer. Chem. Soc., 85, 207 (1963).

The above starting materials of formula 2 and formula 3 are used to prepare the compounds of this invention in the following manner:

The starting material of formula 2 is condensed with substantially one molar equivalent of the starting material of formula 3 to give the corresponding hydrazone of formula 4 in which $R^1$ to $R^5$ inclusive and n are as defined in this first instance.

Generally speaking, the condensation is performed preferably in an inert atmosphere, for example, nitrogen or argon. Although not essential it is convenient to effect the condensation in an inert solvent. Suitable solvents include the lower alkanols such as methanol and ethanol; aromatics such as benzene and toluene; the ethers, such as tetrahydrofuran, diethyl ether, dioxane, bis(2-methoxyethyl)-ether and the like; and the halogenated hydrocarbons, methylene chloride, chloroform and the like. Methanol and ethanol are especially convenient and practical solvents. Times and temperatures for the condensation generally range from 5 minutes to two or three days at 0° to 100° C. Convenient time and temperature ranges include 20° C to the boiling point of the mixture and 15 minutes to 24 hours.

The resulting hydrazone 4 is then cyclized to the tricyclic ester of formula 5 by the action of a suitable cyclization agent according to the conditions of the "Fischer Indole Synthesis," for example, see B. Robinson, Chem. Rev. 63 373 (1963).

A variety of cyclization agents are effective for this cyclization, some of the agents suitable for this cyclization include p-toluenesulfonic acid, hydrogen chloride, hydrogen bromide, phosphoric acid, sulfuric acid, aluminum chloride, zinc chloride, hydrogen bromide in acetic acid, boron trifluoride-etherate, trifluoroacetic acid, cationic ion exchange resins such as Amberlite IR-120, phenyl or ethyl magnesium bromide and aniline salts. In other words the usual catalyst employed for the "Fischer Indole Synthesis" are efficacious; however, the preferred cyclization agents are aqueous solutions of strong acids, for example, 10 to 20% aqueous sulfuric acid, concentrated hydrochloric acid or 10% phosphoric acid.

In practice the isolation of the hydrazone 4 from the condensation reaction mixture is optional. Accordingly, the cyclization agent is added either to the above condensation reaction mixture containing the hydrazone, or to the isolated hydrazone optionally dissolved in one of the above inert solvents, whereby the hydrazone then cyclizes to give the corresponding tricyclic ester of formula 5 in which $R^1$ to $R^5$ inclusive and n are as defined hereinbefore.

The cyclization usually proceeds smoothly and rapidly. Convenient reaction times for the cyclization include five minutes to two hours, preferably five to 30 minutes. Convenient temperaturs include 20° to 200° C, preferably 120° to 180° C.

In practice a most convenient and practical procedure for effecting the above cyclization comprises evaporating solvent from the condensation reaction mixture containing the hydrazone, and then heating the hydrazone at 120° to 200° C in one of the aforementioned solutions of strong acids; the use of an inert solvent during the cyclization being omitted. Incidentally, by following this latter procedure the formation of a by-product of formula 14

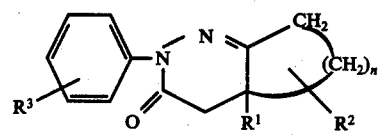

in which $R^1$, $R^2$, $R^3$ and n are as defined in the first instance, occurring when $R^4$ of the hydrazone involved represents hydrogen, is substantially reduced by the use of the higher reaction temperatures and strong acid solutions.

As noted previously the starting material of formula 3 may be either a cycloalkanoneacetic acid derivative ($R^5$ = hydrogen) or its corresponding lower alkyl ester ($R^5$ = lower alkyl). Accordingly, when $R^5$ of the starting material is hydrogen the above process yields the tricyclic compound of formula 5 in which $R^5$ is hydrogen, this compound being identical to the desired compound of formula I; and when $R^5$ of the starting material is lower alkyl the above process yields the tricyclic compound of formula 5 in which $R^5$ is lower alkyl.

The subsequent conversion of the tricyclic compound of formula 5 in which $R^5$ is lower alkyl to the corresponding compound of formula 1 is effected readily by subjecting the tricyclic compound to hydrolysis. Generally speaking, this conversion is most conveniently performed by employing a base as the hydrolyzing agent. The hydrolysis is performed in the presence of sufficient water, followed by acidification of the reaction mixture to yield the desired compound of formula 1. However, the manner of hydrolysis is not intended to be limited to basic hydrolysis since hydrolysis under acidic conditions and other variations, for example, treatment with lithium iodide in collidine (see L. F. Fieser and M. Fieser, "Reagents for Organic Synthesis," John Wiley and Sons, Inc., New York, 1967, pp. 615 – 617) are also applicable.

For basic hydrolysis a preferred embodiment involves subjecting the tricyclic ester to the action of a base, for example, sodium or potassium carbonate, in the presence of sufficient water to effect hydrolysis of the ester. The hydrolysis is performed using a suitable solvent, for example, methanol or ethanol.

The reaction mixture is maintained at a temperature of from 25° C to the reflux temperature until hydrolysis occurs. Usually from 10 minutes to 48 hours is sufficient for this hydrolysis. The reaction mixture is then rendered acidic with an acid, for example, acetic acid, hydrochloric acid, sulfuric acid and the like, to release the free acid as a solid.

Alternatively, the tricyclic ester is hydrolyzed by subjecting the ester to the action of a hydrolyzing agent which is a strong organic or inorganic acid, for example, trifluoroacetic acid, p-toluenesulfonic acid, hydrochloric acid, hydrobromic acid, hydroiodic acid, sulfuric acid, phosphoric acid and the like in a suitable inert solvent at a temperature of at least 60° C and preferably from 90° C to the boiling point of the mixture until the hydrolysis occurs. Usually from 5 to 24 hours are required for this hydrolysis. Suitable solvents include water, acetic acid, aqueous alcohols and the like. If acid hydrolysis is used, the free acid is formed directly. If necessary, the reaction mixture can be diluted with water to precipitate the product.

Finally, it is the intention to cover all changes and modifications of the embodiment of the invention chosen herein for the purpose of disclosure which are within the scope and spirit of this invention. For example, it will be obvious to those skilled in the art that it is not critical to start with a compound of formula 2 in which $R^4$ is lower alkyl in order to prepare a compound of formula 1 in which $R^4$ is lower alkyl. More specifically exemplified, the preceding process readily lends itself to an efficacious modification in which the tricyclic compound of formula 5 in which $R^4$ is hydrogen is subjected to N-alkylation with the appropriate alkyl halide in the presence of one of the aforementioned proton acceptors, preferably sodium hydride, followed by hydrolysis, as described above, of the resulting N-alkylated tricyclic compound of formula 5 to give the corresponding compound of formula 1 in which $R^4$ is lower alkyl. Likewise the preparation of the same compound of formula 1 ($R^4$ = lower alkyl) by a similar N-alkylation of the corresponding compound of formula 1 in which $R^4$ is hydrogen is also intended to be included within the scope and spirit of this invention.

In a related aspect of this invention the tricyclic acetic acid compounds of formula 1 as defined in the first instance as well as the compounds of formula 1 in which $R^1$ is methyl and $R^2$ and $R^3$ are both hydrogen can be converted to corresponding amine derivative of formula 1 in which the acetic acid residue is replaced by a monoalkylamino or dialkylamino residue and $R^4$ is methyl, ethyl or propyl. This conversion can be effected by the methods described in the co-pending Application of Deemerson, et al., Ser. No. 217,627, filed Jan. 13, 1972. For example, the tricyclic acetic acid compound of formula 1 can be reacted with methyl or ethyl chloroformate in the presence of triethylamine to afford the corresponding mixed anhydride which in turn is transformed into the corresponding amide by treatment with the appropriate primary or secondary amine; thereafter, the amide is reduced to the corresponding inodolic amine with a complex metal hydride such as lithium aluminum hydride and said indolic amine is alkylated on the indolic nitrogen by standard methods to yield said corresponding amine. Such corresponding amines include:

1-[2-(dimethylamino)ethyl]-1,2,3,4-tetrahydro-1,9-dimethylcarbazole, nmr CDCl$_3$) δ 1.4 (s, 3H), 2.19 (s, 6H), 3.8 (s, 3H), corresponding hydrochloride salt has m.p. 223°-226° C (dec), 1-[2-(dimethylamino)ethyl]-9-ethyl-1,2,3,4-tetrahydro-1-methylcarbazole, nmr (CDCl$_3$) δ 1.4 (t, J = 7, 3H), 1.4 (s, 3H), 2.2 (s, 6H), corresponding hydrochloride salt has m.p. 206°-209° C, 9-ethyl-1,2,3,4-tetrahydro-1-methyl-1-[2-(methylamino)ethyl]-carbazole, nmr (CDCl$_3$) δ 1.39 (t, J = 7, 3H), 1.41 (s, 3H), 2.37 (s, 3H), corresponding hydrochloride salt has m.p. 213°- 216° C, 1-[2-)dimethylamino)ethyl]-1,2,3,4-tetrahydro-1-methyl-9-propylcarbazole, nmr (CDCl$_3$) δ 1.0 (t, J = 7, 3H), 1.4 (s, 3H), 2.2 (s, 6H), corresponding hydrochloride salt has m.p. 230°- 233° C, 1-[2-(dimethylamino)ethyl]-8,9-diethyl-1,2,3,4-tetrahydro-1-methylcarbazole, nmr (CDCl$_3$) δ 1.18 (t, J = 7, 3H), 1.3 (t, J = 7, 3H), 1.47 (s, 3H), corresponding maleate has m.p. 80°-90° C, and 1-[2-(dimethylamino)ethyl]-1,9-diethyl-1,2,3,4-tetrahydrocarbazole nmr (CDCl$_3$) δ 0.85 (t, 3H), 1.45 (t, 3H), 2.2 (s, 6H), corresponding hydrobromide has m.p. 207°-210° C (dec).

The said corresponding amines are antidepressant agents and are used for this therapeutic purpose in the same manner as described for the amine antidepressants in said co-pending application Ser. No. 217,627. Preferred said amines are those corresponding to the compound of formula 1 in which $R^1$ is methyl and $R^4$ is methyl, ethyl or propyl.

The following examples illustrate further this invention.

EXAMPLE 1

2-Isopropylphenylhydrazine (2, $R^3$ = 2-CH(CH$_3$)$_2$ and $R^4$ = H)

A mixture of the substituted aniline, 2-isopropylaniline (27g, 0.2 mole), concentrated hydrochloric acid (150 ml) and water (160 ml) is stirred mechanically for 30 minutes at room temperature. After cooling to 0° C, the mixture is diazotized by adding dropwise a solution of sodium nitrite (14 g, 0.203 mole) in water (140 ml) over a period of 20 minutes. Stirring is continued for an additional one hour at 0° C. The diazo solution is reduced by adding dropwise a solution of stannous chloride dihydrate (112 g, 0.497 mole) in concentrated hydrochloric acid (90 ml) over a period of 30 minutes at −10° C to −15° C. The reaction mixture is stirred for an additional 1.5 hour at −10° C to −15° C. The precipitate is collected by filtration to give the hydrochloric acid addition salt of the title compound. The salt is purified further by dissolving it in ethanol, concentrating the solution and adding a saturated solution of hydrochloric acid in either to give the hydrochloride salt with mp 206° – 210° C.

By following the procedure of this example and using the appropriate substituted aniline then other substituted hydrazines of formula 2, for example those described as starting materials in Examples 12 - 50 are obtained. More specifically exemplified, the replacement of 2-isopropylaniline with an equivalent amount of 2-propylaniline gives 2-propylphenylhydrazine hydrochloride, mp 182° – 184° C. Similarly, replacement with 2-ethylaniline gives 2-ethylphenylhydrazine hydrochloride, mp 181° – 183° C.

EXAMPLE 2

2-Ethyl-6-(hydroxymethylenecyclohexanone(7, $R^1$ = C$_2$H$_5$, $R^2$ = H, $R^6$ = OH and n = 3)

To a stirred suspension of sodium hydride (18.2 g of 53% oil dispersion, 0.4 mole) in dry ether cooled to 5° under nitrogen, absolute ethanol (2 ml) is added dropwise to initiate the reaction. A solution of the substituted cycloalkanone, 2-ethylcyclohexanone (50.48 g, 0.4 mole), and ethyl formate (48.0 g, 0.6 mole) is then added dropwise over a period of one hr. The mixture is stirred overnight at room temperature. To the stirred yellow suspension absolute ethanol (8 ml) in dry ether (80 ml) is added dropwise. Stirring is continued for one hr, then water (80 ml) is added. The mixture is transferred to separatory funnel, shaken well and the organic layer separated. The organic layer is washed once with water. The aqueous layers are combined, washed once with ether and rendered acidic by the careful addition of 6N HCl.

The acidic solution is extracted with ether (3 x). The ether extracts are washed once with brine, dried (MgSO$_4$) and concentrated. The residue (57.2 g) is distilled give the title compound, bp 82° - 84° C/8mm, nmr (CDCl$_3$) δ 8.65 (s, 1H), 14.70 (broad s, 1H).

EXAMPLE 3

2-[(Butylthio)methylene]-6-ethylcyclohexanone (7, R$^1$ = C$_2$H$_5$, R$^2$ = H, R$^6$ = n—C$_4$H$_9$S and n = 3)

A solution of 2-ethyl-6-(hydroxymethylene)cyclohexanone (43.0 g, 0.277 mole), described in Example 2, butylmercaptan (28.6 g, 0.318 mole) and p-toluenesulfonic acid (50 mg) in dry benzene (200 ml) is heated at reflux under nitrogen for 4 hr using a Dean-Stark water separator. The reaction mixture is cooled and washed with saturated aqueous sodium bicarbonate (50 ml), water and brine, then dried (MgSO$_4$). After removal of the solvent at reduced pressure the residue is distilled to give the title compound, bp 110° - 115° C/1.5 mm, nmr (CDCl$_3$) δ 0.92 (6H), 7.5 (m,1H).

EXAMPLE 4

2-Allyl-2-ethylcyclohexanone (8, R$^1$ —C$_2$H$_5$, R$^2$ = H and n = 3)

Procedure A:

To a well stirred solution of potassium tert-butoxide (17.95 g, 0.16 mole) in dry redistilled tert-butanol (160 ml) nitrogen, 2-[(butylthio)methylene]-6-ethylcylcohexanone (9.05 g, 0.04 mole), described in Example 3, is added slowly. The mixture is stirred at room temperature for 5 minutes and then chilled in an ice bath. Allyl bromide (21.8 g, 0.18 mole) is added rapidly to the chilled mixture. The mixture is then stirred at room temperature for 48 hr. Most of the solvent is then removed under reduced pressure and water (about 150 ml) is added. The aqueous solution is extracted with ether (3 x). The combined ether extracts are washed with brine, dried (MgSO$_4$) and concentrated to yield oil. The oil is subjected to chromotography on silica gel (320 g) using 4% ether in hexane as eluant. Concentration of the eluate gives 2-allyl-6-[(butylthio)methylene]-2-ethylcyclohexanone, nmr(CDCl$_3$) δ 0.85 (t, J=7, 3H), 2.85 (t, J=7, 2H), 4.80 - 6.0 (m, 3H), 7.5 (t, J=2, 1H).

A solution of the latter compound (5.23 g, 0.0196 mole) in 25% NaOH (15 ml) and diethylene glycol (15 ml) is heated at reflux overnight under nitrogen. The camphor smelling mixture is steam distilled and about 250 ml of distillate is collected. The distillate is saturated with NaCl and extracted with ether (4 × 60 ml). The combined ether extracts are washed with 25% aqueous KOH (2 × 10 ml), then brine (2 × 40 ml) and dried (MgSO$_4$). Concentration of the extract affords the title compound as an oil, nmr (CDCl$_3$) δ 0.78 (t, J=7, 3H), 2.15 - 2.4 (m, 4H), 4.8 - 6.1 (m, 3H).

Procedure B:

To a suspension of sodium hydride (55% oil dispersion, 1.74 g, 0.04 mole) in dry dimethoxyethane (75 ml) cooled to 5° C, 2-ethylcyclohexanone (5.04 g, 0.04 mole) is added dropwise over a period of 10 minutes. The reaction mixture is allowed to reach room temperature and then heated to 80° C for one-half hr. The mixture is cooled again at 5° C and allyl bromide (3.45 ml, 4.48g, 0.04 mole) is added dropwise. The mixture is stirred at room temperature for 1 ½ hr. Water (10 ml9 is added dropwise and the mixture transferred to a separatory funnel. It is extracted with ether twice. The ether extracts are dried (MgSO$_4$) and concentrated to give a yellow oil. The oil is subjected to chromatography on silica gel (150 g) using 3% ether in pentane as eluant. The second main product to be eluted is the desired title compound identical to the product obtained by Procedure A.

In a manner similar to that described above under "B", 2-methylcyclopentanone (6.6 g, 0.067 mole) and allyl bromide (9.24 g, 0.07 1 mole) treated in anhydrous ether under nitrogen with sodium tert.-amylate (0.07 mole), worked up as above and purified by distillation, yield 2-allyl-2-methylcyclopentanone as a colourless oil, b.p. 69°-72° C/12 mm νCHCl$_3$/max 1733, 925 cm$^{-1}$, nmr (CDCl$_3$) δ 1.05 (s), 4.85-6.15 (m).

EXAMPLE 5

1-Ethyl-2-oxocyclohexaneacetic Acid (3, R$^1$ = C$_2$H$_5$, R$^2$ and R$^5$ = H and n = 3)

A solution of 2-allyl-2-ethylcyclohexanone (61 g, 0.37 mole), described in Example 4, in reagent acetone is added dropwise under nitrogen to a solution of ruthenium tetroxide (yellow) in carbon tetrachloride prepared as follows:

To ruthenium dioxide (4.7 g) in carbon tetrachloride (600 ml) stirred and cooled (ice bath) under nitrogen, add rapidly sodium metaperiodate (35 g) in water 250 ml. The yellow carbon tetrachloride layer is separated and used as such.

As the addition proceeds, the reaction mixture turns brown, then black as ruthenium dioxide precipitates. Reoxidation to yellow tetroxide is achieved by intermittent addition of sodium metaperiodate in aqueous solution or neat. Total weight of NaIO$_4$ used up: 375 g in about 2 litres of water. Some acetone is added to keep the mixture homogeneous. The temperature rises to 45° C and some cooling is necessary to keep it around 30° C.

The reaction is over after about 4.5 hours. Some isopropanol (50 ml) is added to destroy excess tetroxide. The mixture is filtered through a layer of diatomaceous earth (Celite). The filter cake is thoroughly washed with acetone. The organic layer of the filtrate (CCl$_4$) is concentrated under reduced pressure; the aqueous layer is saturated with sodium chloride and extracted with ether (4x). The combined organic fractions are washed with saturated aqueous sodium bicarbonate (7x). The basic solution is rendered acidic by the careful addition of conc. HCl saturated with sodium chloride and then extracted with ether (4x). The ether extracts are washed once with brine, dried (MgSO$_4$) and concentrated to afford the title compound, $\nu_{max}^{CHCl_3}$ 3400, 1770, 1715 cm$^{-1}$.

In the same manner, but replacing 2-allyl-2-ethylcyclohexanone by 2-allyl-2-methylcyclopentanone described in Example 4 (6.01 g, 0.045 mole), treating the latter compound with ruthenium tetroxide prepared from 2.6 g ruthenium dioxide and working up as described above, there is obtained 1-methyl-2-oxocyclopentaneacetic acid, m.p. 70°-72° C after recrystallization from etherhexane.

The corresponding ethyl ester is obtained by treating the above acid with ethyl bromide and anhydrous potassium carbonate in acetone solution under nitrogeen and purifying by distillation. 1-Methyl-2-oxocyclopentaneacetic acid ethyl ester is obtained as a colourless oil, b.p. 63°-64°C/0.5 mm, $v_{max}^{CHCl_3}$ 1730 cm$^1$, nmr (CDCl$_3$) δ 1.05 (s), 1.22 (t, J=7), 2.36 (d, J=17.5), 2.72 (d, J=17.5), 4.1 (q, J=7), identical with the compound described by L.E. King and R. Robinson in J. Chem. Soc. (1941), 465-470.

EXAMPLE 6

1-Methyl-2-oxocyclohexanepropionic Acid Methyl Ester (9, R$^1$ and R$^7$ = CH$_3$, R$^2$ = H and $n$ = 3)

The substituted cycloalkanone, 2-methylcyclohexanone(160 g. 1.27 mole), is added dropwise to a stirred solution of potassium tert-butoxide (7.0 g, 0.062 mole) in redistilled tert-butanol (325 ml) under nitrogen, followed by the addition of methyl acrylate (102.4 g, 1.20 mole). The temperature is kept below 30° C by intermittent use of a cooling bath. Thereafter the mixture is stirred at room temperature for 2 hr. Dilute sulfuric acid (200 ml) is then added slowly. The aqeuous phase is separated and extracted with ether. The combined organic phases are washed twice with brine, dried (MgSO$_4$) and concentrated to give a crude residue. The residue is fractionated by distillation through a 6 in. Vigreux column. The title compound distills at 106° - 108°/0.4 mm, nmr (CDCl$_3$) δ 1.08 (s, 3H), 1.5 - 2.6 (m, 12 H), 3.66 (s, 3H).

In the same manner but replacing 2-methylcyclohexanone with an equivalent amount of 2-ethylcyclohexanone or 2-propylcyclohexanone, 1-ethyl-2-oxocyclohexanepropionic acid methyl ester, bp 117° - 120° C/0.4mm, and 1-propyl-2-oxocyclohexanepropionic methyl ester, $v_{max}^{CHCl_3}$ 1735, 1700cm$^{-1}$, are obtained, respectively.

EXAMPLE 7

6-Methyl-1,4-dioxospiro[4.5]decane-6-propionic acid methyl ester (10, R$^1$ and R$^7$ = Ch$_3$, R$^2$ = H and $n$ = 3)

A solution of 1-methyl-2-oxocyclohexanepropionic acid methyl ester (96.1 g, 0.48 mole), described in Example 6, ethylene glycol (100 ml) and p-toluenesulfonic acid (2.0 g) in dry benzene (1600 ml) is heated at reflux for 6 hr using a water separator. The benzene solution is cooled, washed with saturated aqueous sodium bicarbonate solution (2 × 100 ml) then brine (2 × 100 ml), dried (MgSO$_4$) and concentrated to yield the title compound as an oil, $v_{max}^{CHCl_3}$ 1725, 1085 cm$^{-1}$.

In the same manner but replacing 1-methyl-2-oxocyclohexane-propionic acid methyl ester with an equivalent amount of 1-ethyl-2-oxocyclohexanepropionic acid methyl ester or 1-propyl-2-oxocyclohexanepropionic acid methyl ester, described in Example 6, 6-ethyl-1,4-dioxospiro[4.5]decane-6-propionic acid methyl ester, $v_{max}^{CHCl_3}$ 1730 cm$^{-1}$ and 6-propyl-1,4-dioxospiro[4.5]-decane-6-propionic acid methyl ester, $v_{max}^{CHCl_3}$ 1735 cm$^{-1}$, are obtained, respectively.

EXAMPLE 8

1-Methyl-2-oxocyclohexaneacetic Acid (3, R$^1$ and R$^5$ = CH$_3$, R$^2$ = H and $n$ = 3

A solution of 6-methyl-1,4-dioxospiro[4.5]decane-6-propionic acid methyl ester (52.5 g, 0.21 mole), described in Example 7, in anhydrous ether (500 ml) and dry benzene (100 ml) is added dropwise under nitrogen to a cooled (0°-5°C) stirred solution of phenylmagnesium bromide in ether prepared from magnesium turnings (15.9 g, 0.65 mole), bromobenzene (75 ml, 0.72 mole) and anhydrous ether (500 ml). (Note: Only about 75 ml of ether is used to start the reaction with 15 drops methyl iodide and 2 - 3 ml bromobenzene). The mixture is stirred overnight at room temperature. Following the careful addition of saturated ammonium chloride solution (114 ml) with cooling, the resulting yellow ether layer is decanted and the precipitated magnesium salts are rinsed thoroughly with ether. The combined ether layers are steam distilled and methanol (100 ml) and 25% aqueous sodium hydroxide (150 ml) is added to the residue. The mixture is heated at reflux for 2 hr to saponify any unreacted ester. The methanol is evaporated and the residue is extracted with ether (4x). The ether extracts are dried (MgSO$_4$) and concentrated to give 6-methyl-α,α-diphenyl-1,4-dioxaspiro[4.5]decane-6-propanol, mp 115°-117° C after recrystallization from chloroformhexane, $v_{max}^{CHCl_3}$ 3620, 3500, 1092 cm$^{-1}$.

The latter compound (35.4 g, 0.07 mole) in acetic acid (500 ml) and water (10 ml) is heated at reflux for 4 hr. Evaporation of the solvents under reduced pressure and repeated evaporation with benzene gives 2-methyl-2-(3,3-diphenylallyl)cyclohexanone as an oil, $v_{max}^{CHCl_3}$ 1740 cm$^{-1}$.

The latter compound (2.40 g, 7.5 mmole) in acetone is oxidized with ruthenium tetroxide-sodium metaperiodate according to the procedure described in Example 5 to give the title compound, mp 87°-90° C after recrystallization from acetone hexane.

In the same manner but replacing 6-methyl-1,4-dioxospiro[4.5]decane-6-propionic acid methyl ester with an equivalent amount of 6-ethyl-1,4-dioxospiro[4.5]decane-6-propionic acid methyl ester, described in Example 7, 1-ethyl-2-oxocyclohexaneacetic acid, identical to the product of the same name of Example 5, is obtained via the respective intermediates, 6-ethyl-α,α-diphenyl-1,4-dioxaspiro[4.5]decane-6-propanol, $v_{max}^{CHCL_3}$ 3450 cm, nmr (CDCl$_3$) δ 0.75 (t, J = 7, 3H), 3.85 (s, 4H), 7.2 - 7.6 (m, 10H) and 2-ethyl-2-(3,3-diphenylallyl)-cyclohexanone, $v_{max}^{CHCl_3}$ 1740 cm$^{-1}$.

Again in the same manner but replacing 6-methyl-1,4-dioxospiro[4.5]decane-6-propionic acid methyl ester with an equivalent amount of 6-propyl-1,4-dioxospiro[4.5]decane-6-propionic acid methyl ester, described in Example 7, 2-oxo-1-propylcyclohexaneacetic acid, $v_{max}^{CHCl_3}$ 1775, 1710 cm$^{-1}$, is obtained via the respective intermediates, α,α-diphenyl-6-propyl-1,6-dioxaspiro[4.5]decane-6-propanol, $v_{max}^{CHCl_3}$ 3620, 3480, 1175, 1130, 1110, 1062 cm$^{-1}$, and 2-(3,3-diphenylallyl)-2-propylcyclohexanone, nmr (CDCl$_3$) δ 0.85 (m, 3H), 6.0 (t, 1H), 7.3 (m, 10H).

EXAMPLE 9

1-Ethyl-2-oxocyclohexaneacetic Acid Methyl Ester (3, R$^1$ = C$_2$H$_5$, R$^2$ = H, R$^5$ = CH$_3$ and n = 3)

To a stirred solution of freshly prepared 1-ethyl-2-oxocyclohexaneacetic acid (680 mg, 3.7 mmoles), described in Examples 5 and 8, under nitrogen at room temperature, anhydrous K$_2$CO$_3$ (773 mg, 5.6 mmoles) and methyl iodide (3.5 ml, 7.98 g, 56 mmoles) are added. The mixture is heated at reflux of 4.5 hr during which time an additional 3 ml of methyl iodide is added every 1.5 hr. Thereafter the solvent is removed at reduced pressure, the residue is partitioned beween ether and cold water. The organic layer is separated, washed with cold water until neutral, then once with brine and dried (MgSO$_4$). Removal of the solvent at reduced pressure affords the title compound, $v_{max}^{CHCl_3}$ 1735, 1705 cm$^{-1}$, nmr (CDCl$_3$) δ 0.8 (t, J=7, 3H), 3.62 (s, 3H).

In the same manner but replacing methyl iodide with an equivalent amount of ethyl iodide or propyl iodide, 1-ethyl-2-oxocyclohexaneacetic acid ethyl ester and 1-ethyl-2-oxocyclohexaneacetic acid propyl ester are obtained, respectively.

In the same manner but replacing 1-ethyl-2-oxocyclohexaneacetic acid with an equivalent amount of 1-methyl-2-oxocyclohexaneacetic acid, described in Example 8, 1-methyl-2-oxocyclohexaneacetic acid methyl ester, $v_{max}^{CHCl_3}$ 1735, 1705 cm, nmr (CDCl$_3$) δ 1.23 (s,3H), 1.8 (m,6H), 2.1 (s, 2H), 2.6 (m,2H), 3.65 (s,3H), is obtained.

In the same manner but replacing 1-ethyl-2-oxocyclohexaneacetic acid with an equivalent amount of 2-oxo-1-propylcyclohexaneacetic acid, described in Example 8, and replacing methyl iodide with an equivalent amount of ethyl iodide, 2-oxo-1-propylcyclohexaneacetic acid ethyl ester, $v_{max}^{CHCl_3}$ 1725, 1705 cm, nmr (CDCl$_3$) δ 0.90 (m,3H), 1.25 (t, J = 7, 3H), 2.52 (d, J = 4, 2H), 4.15 (q, J = 7, 2H), is obtained.

By following serially the procedures of Examples 2,3,4,5 and optionally the procedure of Example 9 and using the appropriate substituted cycloalkanone then other starting materials of formula 3, for example those described as starting materials in Examples 12 - 50 are obtained.

EXAMPLE 10

1,2,3,4-Tetrahydro-1-methylcarbazole-1-acetic Acid Methyl Ester (5, R$^1$ and R$^5$ = CH$_3$, R$^2$, R$^3$ and R$^4$ = H and n = 3)

A solution of the starting material of formula 3, 1-methyl-2-oxocyclohexaneacetic acid methyl ester (18.0 g, 0.097 mole), described in Example 9, and phenylhydrazine (10.6 g, 0.097 mole) in anhydrous ethanol (300 ml) is heated at reflux under nitrogen for 4 hr. Concentration of the reaction mixture affords the corresponding phenylhydrazone of the starting material of formula 3 as a solid, mp 84.5°-86.5° C.

The phenylhydrazone is heated at reflux (bath temp = 150° C) with an excess of 10% aqueous sulfuric acid for 15 minutes. The solution is cooled rapidly, saturated with sodium chloride and extracted with ether (4x). The ether extracts are combined and washed with 5% aqueous NaOH dried (MgSO$_4$) and concentrated. The residue is subjected to chromatography on silica gel using 2.5% acetone in benzene as eluant. Concentration of the eluate gives the title compound, nmr (CDCl$_3$) δ 1.45 (s, 3H), 1.75 - 2.0 (m, 4H), 2.65 (s, 2H), 2.75(m, 2H), 3.68 (s, 3H), 6.9 - 7.6 (m, 4H), 9.2 (s, 1H).

Further elution with the same eluent afforded a small amount of the by-product, 4a-methyl-2-phenyl-4,4a,5,6,7,8-hexahydro-3(2H)-cinnolinone, (14, R$^1$ = CH$_3$, R$^2$ and R$^3$ = H and $n$ = 3), mp 82°-83° C after recrystallization from hexane.

The procedure of Example 10 is followed to prepare other compounds of formula 5 in which R$^1$, R$^2$, R$^3$, R$^4$, R$^5$ and n are as defined in the first instance. For example, by using and equivalent amount of 1-ethyl-2-oxocyclohexane acetic acid methyl ester, described in Example 9, instead of 1-methyl-2-oxocyclohexane acetic acid in the procedure of Example 10, 1-ethyl-1,2,3,4-tetrahydrocarbazole-1-acetic acid methyl ester, (5, R$^1$ = C$_2$H$_5$, R$^2$, R$^3$ and R$^4$ = H, R$^5$ = CH$_3$ and n = 3), mp 67°-71° C after crystallization from benzene, is obtained via the intermediate hydrazone, 1-ethyl-2-oxocyclohexaneacetic acid methyl ester phenyl hydrazone (4, R$^1$ = C$_2$H$_5$, R$^2$, R$^3$ and R$^4$ = H, R$^5$ = CH$_3$ and $n$ = 3), mp 98°-99.5° C after recrystallization from ethanol.

Further examples of such compounds of formula 5 which can be prepared by the procedure of Example 10 are listed in Tables I, II and III. In each of these examples an equivalent amount of the hydrazine of formula 2 and the starting material of formula 3, listed therein, is used in place of the phenylhydrazine and the starting material of formula 3 noted in Example 10.

| | Hydrazine of Formula 2 | | Starting Material of Formula 3 | | | | Product: (Prefix listed below)-1,2,3,4-tetrahydrocarbazole-1-acetic acid (suffix listed below) |
|---|---|---|---|---|---|---|---|
| Ex. | R$^3$ | R$^4$ | R$^1$ | R$^2$ | R$^5$ | n | PREFIX//SUFFIX |
| 11 | H | H | n-C$_3$H$_7$ | H | C$_2$H$_5$ | 3 | 1-propyl//ethyl ester, mp 64–66° C, CHCl$_3$ 3400, 1715 cm$^{-1}$. $v_{max}$ |
| 11a | H | H | n-C$_3$H$_7$ | H | CH$_3$ | 3 | 1-propyl//methyl ester, mp 88–90° C |
| 12 | 2-CH$_3$ | H | CH$_3$ | H | CH$_3$ | 3 | 1,8-dimethyl//methyl ester |
| 13 | 3-C$_2$H$_5$ | CH$_3$ | CH$_3$ | H | CH$_3$ | 3 | 5-(and 7-)methyl-1,9-dimethyl// methyl ester |
| 14 | 4-(i-C$_3$H$_7$) | H | CH$_3$ | H | CH$_2$H$_5$ | 3 | 6-isopropyl-1-methyl//ethyl ester |
| 15 | H | C$_2$H$_5$ | CH$_3$ | H | H | 3 | 9-ethyl-1-methyl//(no suffix) nmr (CDCl$_3$) δ 1.35 (+, J = 7, 3H) 1.4 (s, 3H), 4.3 (q, 2H) |
| 16 | 2-C$_2$H$_5$ | H | C$_2$H$_5$ | H | CH$_3$ | 3 | 1,8-diethyl//methyl ester, mp 91-93° C |
| 17 | 2-(n-C$_3$H$_7$) | H | C$_2$H$_5$ | H | CH$_3$ | 3 | 1-ethyl-8-propyl//methyl ester, mp 99-100° C |
| 18 | 2-(i-C$_3$H$_7$) | H | C$_2$H$_5$ | H | CH$_3$ | 3 | 1-ethyl-8-isopropyl//methyl ester, nmr (CDCl$_3$) δ 0.85 (+, J = 7, 3H) 1.41 (d, J = 7, 6H), 1.8 (m, 6), 2.7 (m, 4), 3.25 (m, 1H), 3.70 (s, 3H), 7.2 (m, 3H), 9.6 (b, 1H) |
| 19 | 2-Cl | H | C$_2$H$_5$ | H | CH$_3$ | 3 | 8-chloro-1-ethyl//methyl ester |
| 20 | 4-F | n-C$_3$H$_7$ | C$_2$H$_5$ | 4-CH$_3$ | H | 3 | 1-ethyl-6-fluoro-4-methyl-9-propyl //(no suffix) |
| 21 | 4-OCH$_3$ | H | C$_2$H$_5$ | H | CH$_3$ | 3 | 1-ethyl-6-methoxy//methyl ester, mp 75-78° C |
| 22 | 3-OC$_2$H$_5$ | H | C$_2$H$_5$ | 5-C$_2$H$_5$ | C$_2$H$_5$ | 3 | 1,3-diethyl-5-(and 7-)ethoxy// ethyl ester |
| 23 | 2-OCOCH$_3$ | H | C$_2$H$_5$ | H | CH$_3$ | 3 | 8-acetoxy-1-ethyl//methyl ester |
| 24 | 4-OCOC$_2$H$_5$ | H | C$_2$H$_5$ | H | CH$_3$ | 3 | 1-ethyl-6-propionoxy//methyl ester |
| 25 | 2-CF$_3$ | C$_2$H$_5$ | C$_2$H$_5$ | H | C$_2$H$_5$ | 3 | 1,9-diethyl-8-trifluoromethyl// ethyl ester |
| 26 | 4-CF$_3$ | H | C$_2$H$_5$ | H | CH$_3$ | 3 | 1-ethyl-6-trifluoromethyl// |

-continued

| | Hydrazine of Formula 2 | | Starting Material of Formula 3 | | | | Product: (Prefix listed below)-1,2,3,4-tetrahydrocarbazole-1-acetic acid (suffix listed below) |
|---|---|---|---|---|---|---|---|
| Ex. | $R^3$ | $R^4$ | $R^1$ | $R^2$ | $R^5$ | n | PREFIX//SUFFIX |
| 27 | H | H | n-$C_3H_7$ | H | H | 3 | 1-propyl//(no suffix), $\nu_{max}^{CDCl_3}$ 3490–3430, 1705 cm$^{-1}$. methyl ester |
| 28 | 2-OH | H | n-$C_3H_7$ | 5-$CH_3$ | $C_2H_5$ | 3 | 8-hydroxy-3-methyl-1-propyl//ethyl ester |
| 29 | 2-$CH_3$ | $CH_3$ | n-$C_3H_7$ | 4-$CH_3$ | $CH_3$ | 3 | 4,8,9-trimethyl-1-propyl//methyl ester |
| 30 | H | H | n-$C_4H_9$ | H | $CH_3$ | 3 | 1-butyl//methyl ester |
| 31 | 2-$C_2H_5$ | H | n-$C_4H_9$ | H | $CH_3$ | 3 | 1-butyl-8-ethyl//methyl ester |
| 32 | n-$C_4H_9$ | H | n-$C_4H_9$ | H | $CH_3$ | 3 | 1,8-dibutyl//methyl ester |

Table II

| | Hydrazine of Formula 2 | | Starting Material of Formula 3 | | | | Product: (Prefix listed below)-1,2,3,4-tetrahydrocyclopent[b]-indole-3-acetic acid (suffix listed below) |
|---|---|---|---|---|---|---|---|
| Ex. | $R^3$ | $R^4$ | $R^1$ | $R^2$ | $R^5$ | n | PREFIX//SUFFIX |
| 33 | H | H | $CH_3$ | H | $C_2H_5$ | 2 | 3-methyl//ethyl ester, $\nu_{max}^{CHCl_3}$ 3440, 1720 cm$^{-1}$ |
| 34 | H | H | $C_2H_5$ | H | $CH_3$ | 2 | 3-ethyl//methyl ester, $\nu_{max}^{CHCl_3}$ 3440, 1730 cm$^{-1}$ |
| 35 | 2-$CH_3$ | H | $C_2H_5$ | H | $CH_3$ | 2 | 3-ethyl-5-methyl//methyl ester |
| 36 | 2-$C_2H_5$ | H | $C_2H_5$ | H | $CH_3$ | 2 | 3,5-diethyl//methyl ester, $\nu_{max}^{CHCl_3}$ 3440, 1722 cm$^{-1}$ |
| 37 | 2-(n-$C_3H_7$) | H | $C_2H_5$ | H | $CH_3$ | 2 | 3-ethyl-5-propyl//methyl ester |
| 38 | 4-Br | $CH_3$ | $C_2H_5$ | H | $CH_3$ | 2 | 7-bromo-3-ethyl-4-methyl//methyl ester |
| 39 | H | H | n-$C_3H_7$ | H | $CH_3$ | 2 | 3-propyl//methyl ester |
| 40 | 4-OH | H | 1-$C_3H_7$ | H | $CH_3$ | 2 | 7-hydroxy-3-isopropyl//methyl ester |
| 41 | H | H | n-$C_4H_9$ | H | $CH_3$ | 2 | 3-butyl//methyl ester |

TABLE III

| | Hydrazine of Formula 2 | | Starting Material of Formula 3 | | | | Product: (Prefix listed below) 5,6,7,8,9,10-hexahydrocyciohept-[b]indole-6-acetic acid (suffix listed below) |
|---|---|---|---|---|---|---|---|
| Ex. | $R^3$ | $R^4$ | $R^1$ | $R^2$ | $R^5$ | n | PREFIX//SUFFIX |
| 42 | H | H | $CH_3$ | H | $C_2H_5$ | 4 | 6-methyl//ethyl ester |
| 43 | 2-$CH_3$ | H | $CH_3$ | H | $C_2H_5$ | 4 | 4,6-dimethyl//ethyl ester |
| 44 | H | H | $C_2H_5$ | H | $C_2H_5$ | 4 | 6-ethyl//ethyl ester |
| 45 | 2-$C_2H_5$ | H | $C_2H_5$ | H | $CH_3$ | 4 | 4,6-diethyl//methyl ester |
| 46 | 4-OCOC$_2$H$_5$ | H | $C_2H_5$ | H | $C_2H_5$ | 4 | 6-ethyl-2-propionoxy//ethyl ester |
| 47 | H | H | $C_2H_5$ | 4-$CH_3$ | $C_2H_5$ | 4 | 6-ethyl-10-methyl//ethyl ester |
| 48 | 4-Cl | H | $C_3H_7$ | H | $C_2H_5$ | 4 | 2-chloro-6-propyl//ethyl ester |
| 49 | 2-(n-$C_3H_7$) | H | n-$C_3H_7$ | H | $C_2H_5$ | 4 | 4,6-dipropyl//ethyl ester |
| 50 | 4-$CH_3$ | $CH_3$ | n-$C_3H_7$ | H | $C_2H_5$ | 4 | 2,5-dimethyl-6-propyl//ethyl ester |

EXAMPLE 51

1,2,3,4-Tetrahydro-1-methylcarbazole-1-acetic Acid (1, $R^1$ = $CH_3$, $R^2$, $R^3$, $R^4$ = H and n = 3)

A mixture of the tricyclic compound of formula 5 having $R^5$= lower alkyl, 1,2,3,4-tetrahydro-1-methyl-carbazole-1-acetic acid methyl ester (5.6 g, 21.8 mmole), described in Example 10, anhydrous potassium carbonate (1.52 g, 11.0 mmole), methanol (65 ml) and water (6.5 ml) is stirred and heated at reflux under nitrogen for 20 hr. Evaporation to dryness of the mixture affords the potassium salt of the title compound. The salt is taken up in water and the solution extracted with ether. The aqueous phase is then rendered acidic with 6N HCl and extracted with ether. This latter extract is washed with brine, dried (MgSO$_4$) and concentrated. The residue crystallized on trituration with a benzene-hexane (4 : 1) mixture to afford the title compound, mp 188°–189°C, $\nu_{max}^{CHCl_3}$ 3410, 1718 cm$^{-1}$.

By following the procedure of Example 51 but using an equivalent amount of the appropriate tricyclic compound of formula 5 having $R^5$ = lower alkyl, for example those described in Example 10 - 50 instead of 1,2,3,4-tetrahydro-1-methylcarbazole-1-acetic acid methyl ester, then the corresponding compounds of formula 1 are obtained. For example by following the procedure of Example 51 but replacing 1,2,3,4-tetrahydro-1-methylcarbazole-1-acetic acid methyl ester with an equivalent amount of 1-ethyl-1,2,3,4-tetrahydrocarbazole-1-acetic acid methyl ester, described in Example 10, 1-ethyl-1,2,3,4-tetrahydrocarbazole-1-acetic acid, mp 148°–150° C after recrystallization from benzene, is obtained.

Examples of other such compounds of formula 1 are listed in Tables IV, V and VI together with the requisite tricyclic compound starting material. In each case the tricyclic compound is noted by the example in which it is prepared.

TABLE IV

| Example | No. of the Example in which the Tricyclic Compound of Formula 5 is Prepared | Product: (Prefix listed below)-1,2,3,4-tetrahydrocarbazole-1-acetic acid |
|---|---|---|
| 52 | 11 | 1-propyl, $v_{max}^{CHCl_3}$ 3490 – 3430, 1740, 1705 cm$^{-1}$, nmr (CDCL$_3$) δ 0.85 (+, j = 7, 3H), 2.7 – 2.75 (s, 4H), 6.9–7.6 (m, 4H) |
| 53 | 12 | 1,8-dimethyl |
| 54 | 13 | 5- (and 7-)ethyl-1,9-dimethyl |
| 55 | 14 | 6-isopropyl-1-methyl |
| 56 | 16 | 1,8-diethyl, mp 119–121° C |
| 57 | 17 | 1-ethyl-8-propyl, mp 127–128° C |
| 58 | 18 | 1-ethyl-8-isopropyl, mp 181–184° C, nmr (CDCl$_3$) δ 0.9 (+, J=7, 3H) 1.35 (d, J=7, 6H), 1.85 (m, 6H) 2.7 (m, 2H), 2.8 (s, 2H), 3.2 (m, 1H), 7.2 (m, 3H), 9.2 (s, 1H), 11.4 (s, 1H) |
| 59 | 19 | 8-chloro-1-ethyl |
| 60 | 21 | 1-ethyl-6-methoxy, mp 95–97° C |
| 61 | 22 | 1,3-diethyl-5-(and 7-)ethoxy |
| 62 | 23 | 8-acetoxy-1-ethyl |
| 63 | 24 | 1-ethyl-6-propionoxy |
| 64 | 25 | 1,9-diethyl-S-trifluoromethyl |
| 65 | 26 | 1-ethyl-6-trifluoromethyl |
| 66 | 28 | 8-hydroxy-3-methyl-1-propyl |
| 67 | 29 | 4,8,9-trimethyl-1-propyl |
| 68 | 30 | 1-butyl-8-ethyl |
| 69 | 31 | 1-butyl |
| 70 | 32 | 1,8-dibutyl |

TABLE V

| Example | No. of the Example in which the Tricyclic Compound of Formula 5 is Prepared | Product: (Prefix listed below)-1,2,3,4-tetrahydrocyclopent [b]-indole-3-acetic acid |
|---|---|---|
| 71 | 33 | 3-methyl, m.p. 146–150° C |
| 72 | 34 | 3-ethyl, m.p. 138–139° C |
| 73 | 35 | 3-ethyl-5-methyl |
| 74 | 36 | 3,5-diethyl, $v_{max}^{CHCl_3}$ 3460, 1705 cm$^{-1}$ |
| 75 | 37 | 3-ethyl-5-propyl |
| 76 | 38 | 7-bromo-3-ethyl-4-methyl |
| 77 | 39 | 3-propyl |
| 78 | 40 | 7-hydroxy-3-isopropyl |
| 79 | 41 | 3-butyl |

TABLE VI

| Example | No. of the Example in which the Tricyclic Compound of Formula 5 is Prepared | Product: (Prefix listed below)-5,6,7,8,9,10-hexahydrocyclohept-[b]indole-6-acetic acid |
|---|---|---|
| 80 | 42 | 6-methyl, m.p. 119–122° C |
| 81 | 43 | 4,6-dimethyl |
| 82 | 44 | 6-ethyl |
| 83 | 45 | 4,6-diethyl, m.p. 103–107° C |
| 84 | 46 | 6-ethyl-2-propionoxy |
| 85 | 47 | 6-ethyl-10-methyl |
| 86 | 48 | 2-chloro-6-propyl |
| 87 | 49 | 4,6-dipropyl |
| 88 | 50 | 2,5-dimethyl-6-propyl |

EXAMPLE 89

1-Ethyl-1,2,3,4-tetrahydro-9-methylcarbazole-1-acetic Acid (1, R$^1$ = C$_2$H$_5$, R$^2$ and R$^3$ = H, R$^4$ = CH$_3$ and n = 3)

A solution of the compound of formula 1, 1-ethyl 1,2,3,4-tetrahydrocarbazole-1-acetic acid (2.0 g, 7.4 mmole), described in Example 51, in dry tetrahydrofuran (THF, 50 ml) is added dropwise under nitrogen to a stirred suspension of sodium hydride (1 g, 50% dispersion, 0.02 mole) in dry THF (25 ml). The reaction mixture is stirred for 15 minutes after the end of the addition. The lower alkyl halide, methyl-iodide (1.5 ml), is added dropwise. The reaction mixture is heated initially to 40° C then stirred for one hour at room temperature. A small amount of water is added cautiously to destroy excess sodium hydride followed by the addition of more water (50 ml). The mixture is washed with ether then rendered acidic and extracted with ether. The ether extract is dried (MgSO$_4$), treated with charcoal and filtered through diatomaceous earth. Evaporation of the ether gives an oil which on recrystallization from benzene affords the title compound, mp 140°–143° C, nmr (CDCl$_3$) δ0.72 (t, J = 7, 3H), 1.9 (m, 6H), 2.75)m, 4H), 3.76 (s, 3H), 7.2 (m, 4H).

By following the procedure of Example 89 and using the appropriate compound of formula 1 in which R$^4$ is hydrogen, for instance those described in Examples 52 – 88, together with the appropriate lower alkyl halide, other compounds of formula 1 in which R$^4$ is lower alkyl are obtained. For example, the use of the compound of formula 1, 1,2,3,4-tetrahydro-1-methylcarbazole-1-acetic acid, described in Example 51, with the lower alkyl halide, ethyl bromide, gives 9-ethyl-1-methyl-1,2,3,4-tetrahydrocarbazole-1-acetic acid, identical to the product of Example 15.

By following the procedure of Example 81 but replacing the compound of formula 1 with an equivalent amount of a compound of formula 5 in which R⁴ is hydrogen and R⁵ is lower alkyl and using the appropriate lower alkyl halide, the corresponding compounds of formula 5 in which R⁴ is lower alkyl and R⁵ is lower alkyl are obtained. More specifically exemplified, by replacing 1-ethyl-1,2,3,4-tetrahydrocarbazole-1-acetic acid with an equivalent amount of 1-ethyl-1,2,3,4-tetrahydrocarbazole-1-acetic acid methyl ester, in the procedure of Example 89, 1-ethyl-1,2,3,4-tetrahydro-9-methylcarbazole-1-acetic acid methyl ester, is obtained.

EXAMPLE 90

5-Ethyl-1,2,3,4-tetrahydro-3-methylcyclopent[b]indole-3-acetic acid (1, $R^1 = CH_3$, $R^2 = H$, $R^3 = 5—C_2H_5$, $R^4 = H$, $n = 2$)

A solution of sodium tert.-amylate in toluene (70 ml, 0.1 mole) is added dropwise with stirring under an atmosphere of nitrogen to a solution of 2-methylcyclopentanone (9.8 g, 0.1 mole) and ethyl bromoacetate (16.7 g, 0.1 mole) in dry benzene (100 ml). The reaction is exothermic, a precipitate is formed, and the mixture turns yellow-orange. Stirring is continued for 3 hrs. at room temperature, the solution is washed with 1% HCl, cold water, and brine, dried over anhydrous magnesium sulfate and the solvent evaporated to yield 1-methyl-2-oxocyclopentane acetic acid ethyl ester as a pale yellow oil which is used without further purification in the subsequent step and which is identical with the same compound described in Example 5.

The above ester (27.78 g, 0.15 mole) and 2-ethylphenylhydrazine hydrochloride (25.89 g, 0.15 mole, prepared as described in Example 1 in dry ethanol (400 ml) is stirred and heated to reflux overnight under nitrogen. The solvent is evaporated, the residue taken up in hot 20% aqueous sulfuric acid (225 ml) and the mixture is stirred at 150° C for one hr., cooled, saturated with sodium chloride, and extracted with ether. After separation of some tarry by-products the ether extracts are washed with water, 5% aqueous sodium hydroxide, water, and brine, dried over anhydrous magnesium sulfate and evaporated. The residue is purified by chromatography on silica gel using benzene-hexane as the solvent, and evaporation of the eluates yields the ethyl ester of the title compound, nmr (CDCl₃) δ 1.25 (t, J=7), 1.50 (t, J=7), 1.50 (s), 4.23 (t, J=7), 6.95 - 7.4 (m), 8.8 (broad).

A mixture of the above ethyl ester (2.55 g, 0.0095 mole) potassium carbonate (1.5 g, 0.011 m) methanol (60 ml), and water (10 ml) is stirred under nitrogen and heated to reflux for 19 hrs. Evaporating the solvent, dissolving the residue in water (50 ml), extraction with ether, acidifying the aqueous phase with dilute hydrochloride acid, saturating with sodium chloride, extracting with ether containing a small amount (50 mg) of 2,6-di-tert-butyl-p-cresol ("Ionol" as anti-oxident, drying over anhydrous magnesium sulfate and evaporating yields the title compound with m.p. 124–129° C after crystallization from hexane, nmr (CDCl₃) 1.35 (t, J=7), 1.4 (s), 2.2 - 3.0 (m), 6.9 - 7.45 (m), 8.5 (s), 10.4 (broad).

EXAMPLE 91

8-Butyl-1-ethyl-1,2,3,4-tetrahydrocarbazole-1-acetic acid (1, $R^1 = C_2H_5$, $R^2 = H$, $R^3 = 8—n—C_4H_9$, $R^4 = H$, $n = 3$)

A mixture of 2-butylphenylhydrazine (prepared from 10.0 g of the hydrochloride salt, 0.05 mole, obtained from 2-butylaniline and sodium nitrite in a similar manner to that described in Example 1) and 1-ethyl-2-oxocyclohexaneacetic acid methyl ester (10.0 g, 0.05 mole, prepared as described in Example 9) in ethanol (50 ml) is heated to reflux under an atmosphere of nitrogen for 24 hrs. The mixture is cooled, the solvent evaporated, and the residue is heated to reflux (bath temperature 160° C) with 20% aqueous sulfuric acid (100 ml) under nitrogen for 30 minutes. The mixture is poured on crushed ice, extracted with ether, the ether extracts washed with 5% sodium hydroxide solution and evaporated. The residue is purified by chromatography on silica gel using benzene-hexane (1:1) as the eluant and evaporation of the eluates yields the methyl ester of the title compound as an oil.

The above methyl ester (3.8 g, 0.011 mole), potassium carbonate (2.0 g, 0.014 mole) is methanol (100 ml) and water (10 ml) is stirred under nitrogen and heated to reflux for 20 hrs. Evaporation of the solvent, addition of water (50 ml), acidification with 6N hydrochloric acid (15 ml) and extraction with ether, drying the ether extracts over magnesium sulfate, filtering through activated carbon and evaporating yields the title compound, m.p. 131°-134° C after recrystallization from hexane, nmr (CDCl₃) δ 0.9 (m), 7.2 (m), 8.8 (s), 10.6 (broad).

EXAMPLE 92

4-Ethyl-5,6,7,8,9,10-hexahydro-6-methylcyclohept[b]indole-6-acetic acid (1, $R^1 = CH_3$, $R^2 = H$, $R^3 = 4—C_2H_5$, $R^4 = H$, $n = 4$)

A mixture of cycloheptanone pyrrolidine enamine (151.0 g, 0.92 mole) and chloroacetonitrile (151.0 g, 2 moles) in dry, peroxide-free dioxane is heated to reflux under nitrogen for 3 hrs. The reaction mixture is cooled, poured into ice, extracted with ether, the combined ether extracts washed with 1N hydrochloric acid, water and saturated sodium chloride solution, and dried over magnesium sulfate. Evaporation of the solvent and distillation of the residue yields 2-cyanomethylcycloheptanone, bp 162°-165° C/16 mm, $\nu_{max}^{CHCl_3}$ 2240, 1700 cm⁻¹, nmr (CDCl₃) δ 1.8 (m), 2.4 - 3.1 (m).

A solution of sodium tert.-amylate in toluene (340 ml, 0.297 mole) is added dropwise with stirring under nitrogen to a solution of 2-cyanomethylcycloheptanone (44.6 g, 0.297 mole, obtained as described above) and methyl iodide (42.6 g, 0.3 mole) in dry benzene (200 ml), and the mixture is stirred at 65° C for 4 hrs. and allowed to stand overnight at room temperature. The reaction mixture is washed with 1% aqueous hydrochloric acid, water, saturated sodium chloride solution, dried over magnesium sulfate, and the solvent is evaporated. Distillation of the residue under reduced pressure yields 2-cyanomethyl-2-methylcycloheptanone, bp. 152°-158° C/14 mm, nmr (CDCl₃) δ1.27 (s, 3H).

A solution of 2-methyl-2-cyanomethylcycloheptanone described above (34.3 g, 0.208 mole) in 10% aqueous sodium hydroxide (500 ml) is heated to reflux for 3 hrs., cooled, washed with ether, acidified with 6N hydrochloric acid, saturated with sodium chloride and extracted with ether. The ether phase is separated, washed with saturated sodium chloride solution, dried over magnesium sulfate and evaporated to yield 1-methyl-2-oxocycloheptaneacetic acid, m.p. 43–45° C after crystallization from ether-hexane, $\nu_{max}^{CHCl_3}$ 2900, 1705 cm⁻¹, nmr (CDCl₃) δ1.25 (s), 1.65 (m), 2.58 (m), 10.1 (s).

A mixture of 1-methyl-2-oxocycloheptaneacetic acid (3.0 g, 0.0163 mole, obtained as described above), anhydrous potassium carbonate (2.76 g, 0.020 mole) and methyl iodide (8 ml) in acetone (50 ml) is stirred and heated to reflux for 2 hrs. Methyl iodide (3ml) is added and heating to reflux is continued for another 3 hrs. The solvent is evaporated, the residue taken up in water (50 ml), saturated with sodium chloride, and extracted with ether. The combined ether extracts are washed with saturated sodium chloride solution, dried over magnesium sulfate and evaporated to yield 1-methyl-2-oxocycloheptaneacetic acid methyl ester as an oil, $v_{max}^{CHCl_3}$ 1730, 1700 cm$^{-1}$, nmr (CDCl$_3$) $\delta$1.2 (s), 3.67 (s).

A mixture of 1-methyl-2-oxocycloheptaneacetic acid methyl ester (5.0 g, 0.025 mole), 2-ethylphenylhydrazine (prepared from 4.4 g of the hydrochloride salt, 0.025 mole) and 2-ethylphenylhydrazine hydrochloride (3.0 g, 0.017 mole, prepared as described in Example 1) in anhydrous ethanol (35 ml) is stirred and heated to reflux under nitrogen for 18 hrs. The reaction mixture is cooled, the solvent evaporated, and the residue is heated to reflux (bath temperature 160°-180° C) under nitrogen with 20% aqueous sulfuric acid (50 ml) for 45 minutes. The reaction mixture is poured on ice, extracted with ether, the ether extracts washed with saturated sodium chloride solution, dried over anhydrous magnesium sulfate, evaporated to dryness, and the residue is passed through a column of silica gel. Elution with benzene followed by benzene containing 2% acetone and evaporation of the eluates yields the methyl ester of the title compound as an oil, nmr (CDCl$_3$) $\delta$ 1.25 (m), 1.50 (s), 1.90 (m), 2.85 (m), 3.65 (s), 7.0 – 7.5 (m).

The methyl ester of the title compound obtained as described above (1.0 g), potassium carbonate (0.6 g), methanol (30 ml), and water (5 ml) is stirred and heated to reflux under nitrogen for 20 hrs. The reaction mixture is concentrated to one-half volume, water is added, and the mixture is washed with ether. The aqueous layer is acidified with 6N hydrochloric acid and extracted with ether, the ether extracts dried, filtered through activated carbon, and evaporated to yield the title compound, m.p. 148°-151° C after recrystallization from ether-hexane, nmr (CDCl$_3$) $\delta$ 1.35 (t, J=7), 1.55 (s), 1.9 (m), 2.8 (m), 7.0 – 7.5 (m), 8.5 (s), 11.3 (s).

We claim:
1. 1-Ethyl-1,2,3,4-tetrahydrocarbazole-1-acetic acid.
2. 1-Propyl-1,2,3,4-tetrahydrocarbazole-1-acetic acid.
3. 1,8-Diethyl-1,2,3,4-tetrahydrocarbazole-1-acetic acid.
4. 1-Ethyl-8-propyl-1,2,3,4-tetrahydrocarbazole-1-acetic acid.
5. 1-Ethyl-8-isopropyl-1,2,3,4-tetrahydrocarbazole-1-acetic acid.
6. 1-Ethyl-1,2,3,4-tetrahydro-9-methylcarbazole-1-acetic acid.
7. 9-Ethyl-1-methyl-1,2,3,4-tetrahydrocarbazole-1-acetic acid.
8. 8-Butyl-1-ethyl-1,2,3,4-tetrahydrocarbazole-1-acetic acid.

* * * * *